United States Patent
Strohmayr et al.

(10) Patent No.: US 9,364,203 B2
(45) Date of Patent: Jun. 14, 2016

(54) MINIMALLY INVASIVE INSTRUMENT

(75) Inventors: Michael Strohmayr, München (DE); Sophie Lantermann, München (DE); Florian Alexander Fröhlich, München (DE)

(73) Assignee: Deutsches Zentrum für Luft- und Raumfahrt e.V., Köln (DE)

( * ) Notice: Subject to any disclaimer, the term of this patent is extended or adjusted under 35 U.S.C. 154(b) by 496 days.

(21) Appl. No.: 13/816,431

(22) PCT Filed: Aug. 18, 2011

(86) PCT No.: PCT/DE2011/001614
§ 371 (c)(1), (2), (4) Date: Apr. 18, 2013

(87) PCT Pub. No.: WO2012/037917
PCT Pub. Date: Mar. 29, 2012

(65) Prior Publication Data
US 2013/0197493 A1 Aug. 1, 2013

(30) Foreign Application Priority Data

Aug. 18, 2010 (DE) .................... 10 2010 034 712
Aug. 18, 2010 (DE) .................... 10 2010 034 717
Aug. 18, 2010 (DE) .................... 10 2010 034 719

(51) Int. Cl.
*A61B 17/00* (2006.01)
*G01L 5/22* (2006.01)
*G06F 3/01* (2006.01)
*A61B 17/02* (2006.01)

(52) U.S. Cl.
CPC ........... *A61B 17/00234* (2013.01); *G01L 5/228* (2013.01); *G06F 3/016* (2013.01); *A61B 2017/0003* (2013.01); *A61B 2017/00039* (2013.01); *A61B 2017/00526* (2013.01); *A61B 2017/0212* (2013.01); *A61B 2562/02* (2013.01); *A61B 2562/046* (2013.01); *A61B 2562/164* (2013.01)

(58) Field of Classification Search
None
See application file for complete search history.

(56) References Cited

U.S. PATENT DOCUMENTS

| 4,492,949 A | 1/1985 | Peterson et al. |
| 7,898,381 B2 * | 3/2011 | Hatsuda .................... 338/47 |
| 8,033,189 B2 * | 10/2011 | Hayakawa et al. ......... 73/865.7 |

(Continued)

FOREIGN PATENT DOCUMENTS

DE         43 32 580 A1      3/1995

OTHER PUBLICATIONS

International Preliminary Report on Patentability and Written Opinion issued in PCT/DE2011/001614 on Feb. 28, 2013.

*Primary Examiner* — Robert R Raevis
(74) *Attorney, Agent, or Firm* — Hoffmann & Baron, LLP

(57) ABSTRACT

The invention relates to a minimally invasive instrument comprising an enlargeable sensor head with a flat sensor element that has resilient properties. In order to enable an improved minimally invasive instrument, the sensor element comprises a film element with a first layer and with a second layer distanced from the first layer by means of spacers, wherein the sensor element comprises, arranged between the layers of the film element, expansion-sensitive, polymer-based resistance elements for picking up tactile stimuli.

12 Claims, 9 Drawing Sheets

(56) References Cited

U.S. PATENT DOCUMENTS 8,371,174 B2 * 2/2013 Chen et al. .................. 73/727
8,448,530 B2 * 5/2013 Leuenberger et al. ... 73/862.625
2007/0227267 A1 10/2007 Loeb et al.

* cited by examiner

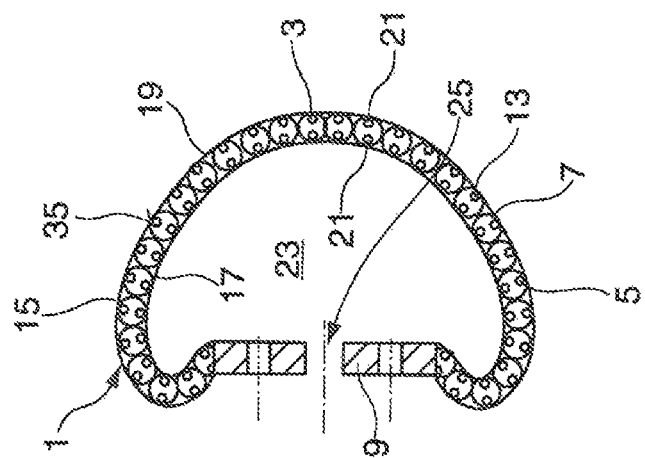
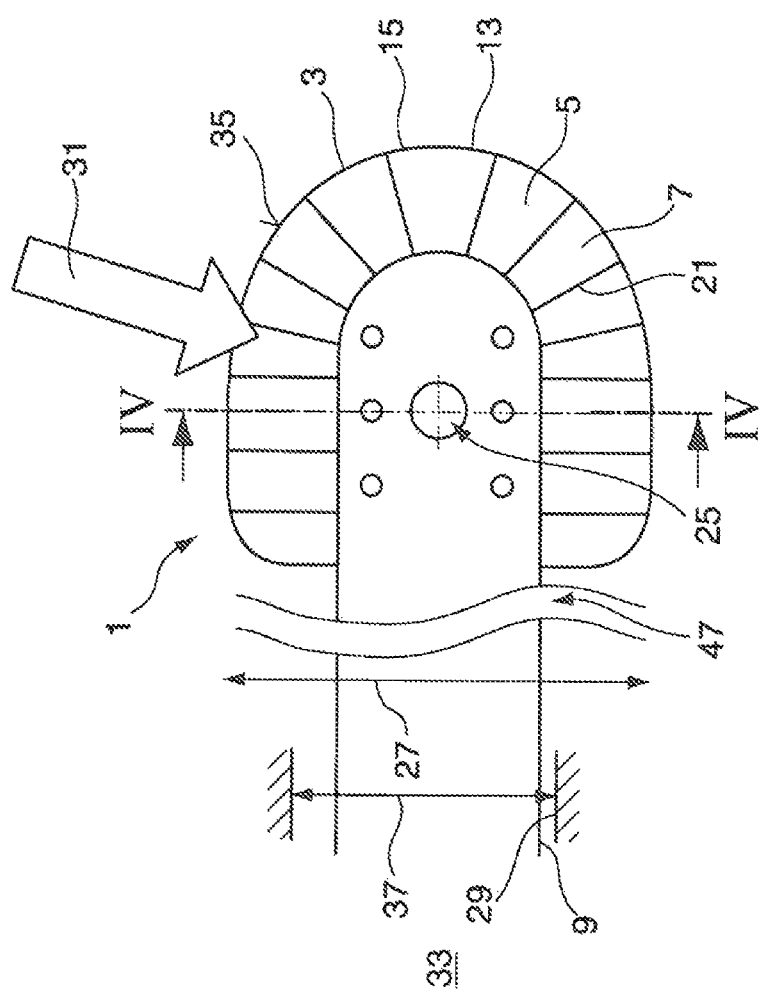

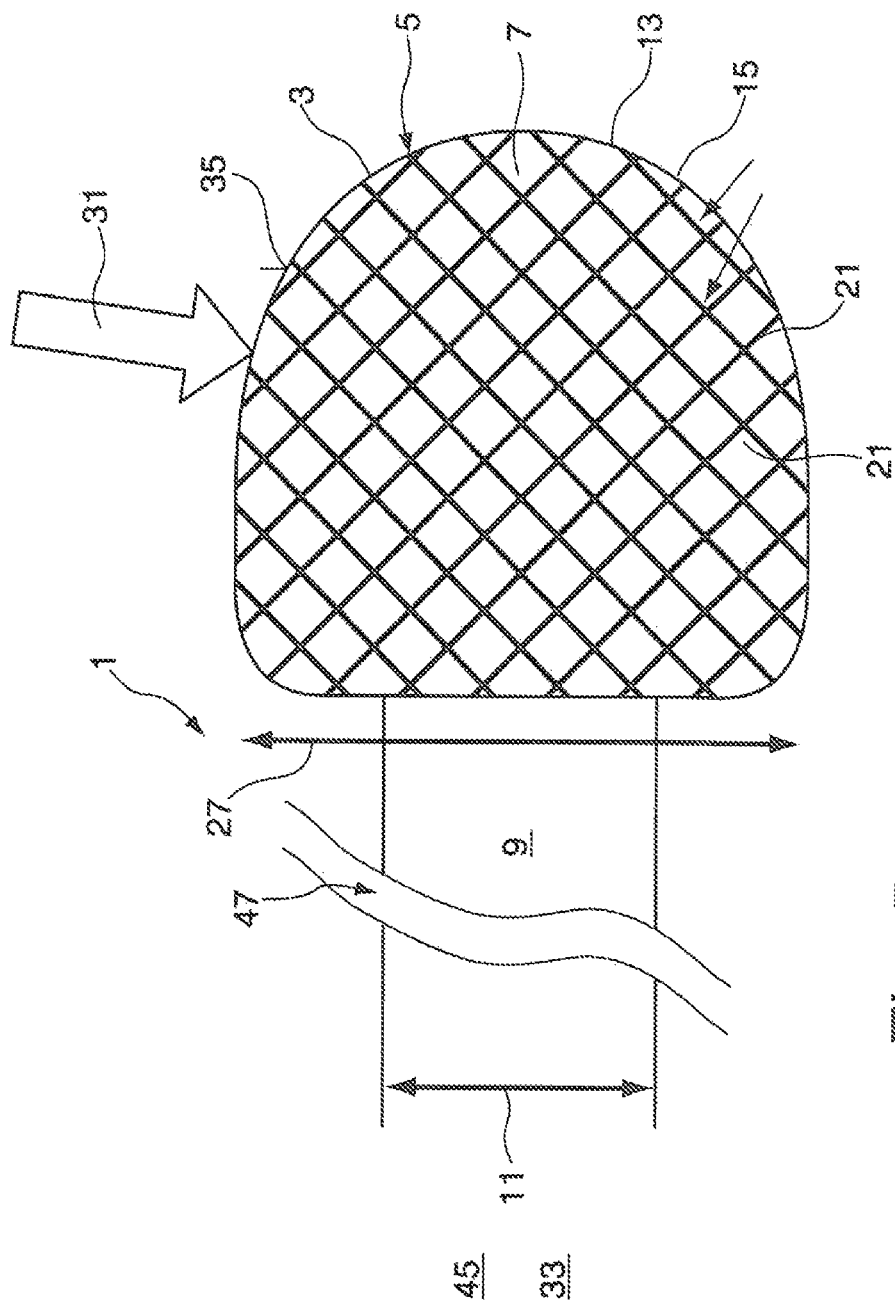

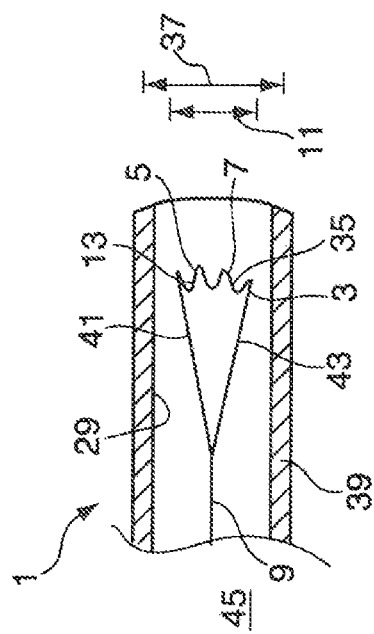
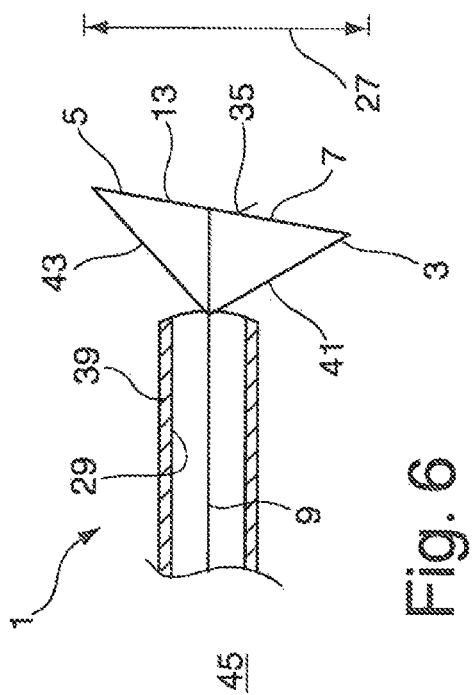

US 9,364,203 B2

MINIMALLY INVASIVE INSTRUMENT

CROSS-REFERENCE TO RELATED APPLICATIONS

This application is the U.S. National Phase of, and Applicant claims priority from, International Application No. PCT/DE2011/001614 filed 18 Aug. 2011, German Patent Application No. DE 10 2010 034 719.1, filed 18 Aug. 2010, German Patent Application No. DE 10 2010 034 717.5, filed 18 Aug. 2010, and German Patent Application No. DE 10 2010 034 712.4, filed 18 Aug. 2010, each of which is incorporated herein by reference in its entirety.

BACKGROUND

The invention relates to a minimally invasive instrument, by means of which a procedure can be carried out through an access channel, said instrument having a distal end that can be inserted into the access channel and a tactile sensor assigned to the distal end, by means of which tactile stimuli can be detected during the procedure.

Minimally invasive instruments are known. These normally have a distal end, which can be guided through a relatively small access channel, wherein a procedure can be carried out by means of the distal end. The access channel may be formed by a trocar for example. Such minimally invasive instruments can be used for example for examinations and/or minimally invasive interventions. Such minimally invasive instruments can be guided manually or in a robot-assisted manner. DE 10 2007 037 262 B3 relates to a force moment sensor for measuring at least three orthogonal loads. Rod-like elements in the form of glass fibres without a supporting structure are provided to measure at least three orthogonal loads and are fixed in platforms. Rod-like portions alternatively and/or additionally form one continuous glass fibre or a few glass fibres, which are wound helically about a virtual cylinder. A coating may be applied to the glass fibres. The force moment sensor may be used in gripping devices, which are used in medical engineering. The force moment sensor may also be used in instruments that are used in minimally invasive surgery.

SUMMARY

The object of the invention is to provide an improved minimally invasive instrument, and in doing so in particular to enable improved tactile sensing.

The object is achieved in the case of a minimally invasive instrument having an enlargeable sensor head with a flat sensor element having resilient properties in that the sensor element comprises a film element with a first layer and with a second layer distanced by means of spacers from the first layer, wherein the sensor element has, arranged between the layers of the film element, expansion-sensitive, polymer-based resistance elements for picking up tactile stimuli. The sensor head comprises a tactile sensor. The tactile sensor comprises the sensor element. The tactile stimuli can advantageously be sensed or picked up by means of the polymer-based resistance elements, wherein the tactile stimuli lead to expansions of the polymer-based resistance elements or can be converted into such expansions. The expansions of the polymer-based resistance elements in turn cause a change to a conductivity, which in turn can be converted into an electrical resistance signal, for example a voltage and/or a current, by connecting an evaluation unit accordingly. The film element comprises the resiliently deformable first layer with a first surface and the resiliently deformable second layer with a second surface, wherein the first and the second surface face one another, are distanced from one another by resiliently deformable spacers arranged individually between the first and second surface, and are interconnected, and defined gaps/cavities are formed between the spacers and the first and second surface. A procedure can be carried out through an access channel by means of the minimally invasive instrument. Said instrument comprises a distal end, which can be inserted into the access channel, and a tactile sensor of the sensor head assigned to the distal end, by means of which tactile stimuli can be detected during the procedure. The tactile sensor comprises the flat sensor element having resilient properties with a tactilely sensitive surface that can be passed through the access channel and provided thereafter, wherein, in a provided state, a two-dimensional expansion of the tactilely sensitive surface exceeds a dimension of a cross section of the access channel. The tactilely sensitive surface may advantageously be provided after insertion through the relatively narrow access channel, in such a way that the two-dimensional expansion exceeds the dimension of the cross section of the access channel. A dimension of the access channel cross section may be understood for example to mean a height, a width, a surface area, in the case of a circular access channel a diameter, and/or a similar dimension. Furthermore, "exceed" may be understood to mean that the tactilely sensitive surface cannot pass through the access channel in a collision-free manner in the provided state. The relatively large tactilely sensitive surface may advantageously be provided in spite of the relatively small access channel, wherein the tactile stimuli can advantageously be picked up simultaneously by a larger surface. The procedure can be understood for example to mean a palpation of tissue, wherein, for this purpose, the tactile sensor or the tactilely sensitive surface of the tactile sensor can be brought into bearing contact with the tissue to be palpated, such that tactile stimuli can be transferred. This can be achieved for example by corresponding manipulation of the minimally invasive instrument, for example guided manually and/or in a robot-assisted manner. Alternatively and/or additionally, the procedure may be understood to mean a lifting and/or positioning of tissue, in particular of an organ. Tactile stimuli for palpating the tissue and/or tactile stimuli for monitoring a contact pressure during the lifting and/or the positioning of the tissue, in particular of the organ, may advantageously occur during the procedure. The expression "assigned to the distal end" may be understood to mean that the tactile sensor is arranged at the distal end. The tactile sensor may in particular make up the distal end and/or the distal end may comprise the tactilely sensitive surface of the tactile sensor.

In accordance with an exemplary embodiment of the instrument, the tactilely sensitive surface can be provided by means of a stretching device. The sensor element of the tactile sensor may advantageously be stretched by means of the stretching device after insertion or guidance through the access channel, such that the relatively large tactilely sensitive surface is provided.

In accordance with a further exemplary embodiment of the instrument, the sensor element surrounds a cavity in a fluid-tight manner, at least in part. The cavity may advantageously recede during the guidance through the access channel and due to the resilient properties of the sensor element, wherein the relatively large tactilely sensitive surface is provided by restoring forces after insertion through the access channel.

In accordance with a further exemplary embodiment of the instrument, the treatment device has a fluid flow source, which is assigned to the cavity by means of a fluid path. The fluid flow source is advantageously a pump that is provided anyhow with minimally invasive instruments, in particular a bidirectional pump, suction pump and/or force pump. The cavity may advantageously be inflated or emptied selectively by means of the fluid flow source. The fluid flow source may be adapted to convey any fluid, for example a liquid, in particular water. The fluid may alternatively and/or additionally be air. The fluid flow source may alternatively be understood to be a fluid store or a fluid source subject to excess pressure or negative pressure, for example a compressed gas connection, a water connection, or the like. The term "fluid flow source" is therefore to be interpreted broadly, in particular as the source of a fluid flow, wherein a direction of the fluid flow or a pressure differential that drives the fluid flow and indicates the direction is not determined.

In accordance with a further exemplary embodiment of the instrument, the cavity is surrounded in a fluid-type manner partly by a shaft and partly by the sensor element. The sensor element may advantageously have a two-dimensional expansion, in particular similarly to a film assigned in a fluid-tight manner to the distal end. The cavity is thus provided within an outer face of the shaft and of the sensor element. This cavity may advantageously be filled with the fluid at a specific pressure, wherein the sensor element advantageously develops hydrostatic forces occurring accordingly during this process, wherein the relatively large tactilely sensitive surface is thus provided.

In accordance with a further exemplary embodiment of the instrument, the fluid path discharges into the cavity. The fluid may advantageously be introduced into the cavity or removed therefrom selectively, in particular sucked up therefrom, via this fluid path.

The gaps are preferably filled with a fluid medium, wherein, in the present case, a fluid medium is understood to mean a substance that does not pose any resistance to an arbitrarily slow shear force and thus has finite viscosity. Fluid media therefore in particular comprise gases and liquids, but also gels. Furthermore, the gaps in the film element may be open or closed on the whole with respect to a surrounding environment of the film element, that is to say in the first case the fluid medium may escape from the film element or may penetrate the film element, and in particular the outer pressure (for example atmospheric pressure) is the same as the inner pressure in the gaps, whereas in the second case the fluid medium is trapped in the gaps. The selection of the fluid medium and the embodiment (outwardly closed/open gaps) influence the resilient properties of the film element and may be selected in accordance with the requirements.

Due to the use of individually arranged, resiliently deformable spacers between the two layers of the film element, the material volume that has to be deformed under the action of an application of mechanical force is reduced. Furthermore, a geometrically known density distribution in the film element is provided by the known gaps, such that the hysteresis behaviour of the film element in the event of mechanical deformation can be controlled. Anisotropic resilient deformation behaviour can additionally be set, that is to say the volume to be deformed can be freely defined and arranged in the film element as a result of a corresponding arrangement of the spacers. When using the film element with the tactile sensor, the sensitivity of the sensor can thus be adapted to the object to be achieved, for example high sensitivity to perpendicular forces with simultaneously low sensitivity to horizontal forces and vice versa. The spacers may advantageously have a cross section deviating from a circular shape, for example an oval, polygonal or rectangular cross section. Shear forces (caused by a tactile stimulus) acting on individual spacers thus experience direction-dependant counter forces of different strength. The anisotropic behaviour can thus advantageously be achieved in addition to other measures.

In addition to tactile sensors, the film element can also be used for passive/active vibration dampers, or with grippers or gripping tools. If the gaps are filled with an electrorheological liquid, a two-dimensional damping element with damping behaviour that can be set locally can be produced. If the spacers are produced for example from electroactive polymers, an active two-dimensional damping/actuator element can be produced.

The film element can be produced by the following steps: providing a resiliently deformable first layer with a first surface, applying first spacers made of a curable polymer material in a first arrangement to the first surface, providing a resiliently deformable second layer with a second surface, joining the second surface to the first spacers at the ends thereof remote from the first surface, moving the first and second layer away from one another such that the first and second surface are arranged at a predefined distance from one another and the first spacers connect the first and second surface, curing the first spacers, wherein the polymer material of the first spacers is resiliently deformable after curing and the first spacers, in a mechanically unstressed state, distance the first and second surface by a distance A. The spacers are preferably arranged individually. They may be shaped arbitrarily (linear, star-shaped, dot-shaped, etc.), and in particular may also be contiguous and/or formed as closed shapes, for example as a circle or oval, etc.

The first and second layer provided each preferably consist of a polymer material, for example a thermoplastic material in particular of a silicone material, and preferably have a layer thickness of <15 mm, <10 mm, <5 mm, <2 mm, <1 mm, <0.5 mm, <0.1 mm, or <0.05 mm. Of course, the layer thickness of the first and second layer can be selected differently as required.

The curable polymer material of the first spacers is preferably likewise a thermoplastic material, or a silicone material, wherein, in the present case, the term "curable" is understood to mean that the polymer material of the first spacers is not yet completely cross-linked, or is not yet completely vulcanised, or is not yet completely cured or cooled at the moment of application to the first surface. The first spacers or the curable polymer material is preferably applied by means of a pressing, compression-moulding, casting, injection-moulding, doctoring or calendering process. The first surface and the applied first spacers are bonded after application thereof, a chemical or thermal pretreatment (heating) of the first surface possibly being necessary for this purpose.

Depending on requirements, like or different resilient materials can be used for the first layer, the second layer and the first spacers to set a predetermined deformation behaviour of the film element. The direction-dependant (anisotropic) deformation behaviour of the film element can also be set by the selection of the first arrangement of the first spacers on the first surface. The arrangement of the first spacers preferably has a trapezoidal, annular, elliptical or rectangular, in particular square, geometry. Any other first arrangements can of course be implemented depending on requirements.

Once the first spacers have been applied to the first surface and have been bonded therewith, the second resiliently deformable layer with a second surface is advantageously provided. The second surface is then joined to the first spacers at the ends thereof remote from the first surface. During the joining process, the polymer material of the first spacers connects fixedly to the second surface. A physical, chemical or thermal pretreatment of the second surface may likewise be necessary for this purpose. After this method step, a type of "sandwich film" or a film composite is produced, which comprises the first layer, the second layer, and first spacers arranged therebetween. Gaps are formed between the spacers, the first surface, and the second surface.

Once the first spacers have bonded with the second surface, the first and second layer are moved away from one another, such that the first and second surface are arranged at a predefined distance from one another and the first spacers connect the first and second surface. The predefined distance is in any case to be selected such that the first spacers still connect the first and second surface, that is to say do not tear or detach from one or both of the first and second surfaces. The outer shapes of the first spacers are changed by moving the first and second layer away from one another. A cylindrical outer contour of the first spacers or an outer contour of the first spacers in the form of a hyperboloid of one sheet is typically set in this instance. Furthermore, the size of the gaps formed between the first spacers and the first and second surface is set by moving the first and second layer away from one another. The setting of the shape of the first spacers and of the size of the gaps may in turn predefine or set the direction-dependant (anisotropic) deformation behaviour of the film element.

The first and second layer can be moved away from one another for example by means of two perforated plates, which are connected to a vacuum pump to generate negative pressure at one of their respective surfaces. These surfaces are brought into contact with surfaces of the first and second layer opposite the first and second surface respectively. The first and second layer adhere to the perforated plates due to the negative pressure and can be selectively distanced from one another by moving the plates away from one another accordingly.

Once the plates have been moved away from one another, the first spacers are cured, wherein the polymer material of the spacers is resiliently deformable after curing and the spacers, in a mechanically unstressed state, distance the first and second surface by a distance A. In the present case, the term "curing" is used in the sense of "cross-linking", "vulcanising", "setting", or "cooling" depending on the polymer material used. Once cured, the polymer material of the first spacers is resiliently deformable and is substantially dimensionally stable.

In an advantageous development of the method, the composite formed of spacers and the first and second layer is heated before the layers are moved away from one another and is cooled once said layers have been moved away from one another.

The film element, that is to say the laminate formed of the first and second layer with the intermediate first spacers, preferably has a (film element) thickness of <50 mm, <25 mm, <10 mm, <5 mm, <2 mm, <1 mm, <0.5 mm, or <0.1 mm. Furthermore, the distance A is preferably <15 mm, <10 mm, <5 mm, <3 mm, <2 mm, <1 mm, <0.5 mm, or <0.2 mm. Of course, the selections of the layer thicknesses of the first and second layer, of the distance A, and of the shape and mass of the individual first spacers are dependent on one another and on the current objective, and therefore these cannot be selected arbitrarily, but can be easily selected by a person skilled in the art.

The resiliently deformable film element produced by means of the method has two layers (the first and the second layer), which are distanced from one another by a distance A by intermediate, individually arranged, correspondingly shaped spacers. The properties of the mechanical resilient deformability of the film element can be set by suitable selection of the resilient materials involved, the first arrangement of the first spacers, the distance A, and the shape of the first spacers produced by moving the first and second layer away from one another.

In accordance with an alternative, the film element can be produced by the following steps: providing a resiliently deformable first layer with a first surface, applying individual second spacers made of a curable polymer material in a second arrangement to the first surface, providing a resiliently deformable second layer with a second surface, applying individual third spacers made of a curable polymer material in a third arrangement, which is axially symmetric relative to the second arrangement, to the second surface, aligning the first and second layer so that the arrangements of the second and third spacers applied to the first and second surface are congruently opposed, joining the congruently opposed second and third spacers at their respective free ends, moving the first and second layer away from one another such that the first and second surface are arranged at a predefined distance from one another and the spacers connect the first and second surface, and curing the spacers, wherein the polymer material of the spacers is resiliently deformable after curing and the spacers, in a mechanically unstressed state, distance the first and second surface by a distance A.

In contrast to the method described beforehand, the spacers in this method alternative are not only applied to the surface of the first layer, but the final spacers are formed from two parts: the second and third spacers, which are applied in a mirror-inverted arrangement to the first and second surface. The alignment of the first and second layer is therefore advantageously necessary in this method so that the arrangements of the second and third spacers applied to the first and second surface are congruently opposed. The first and second layer provided are connected in this case by joining the congruently opposed second and third spacers at their respective free ends. The spacers are preferably treated thermally, chemically, mechanically, with electromagnetic radiation, with plasma, or with particle radiation before being joined so as to promote the joining of the spacers and/or a change in shape of the spacers whilst the first and second layer are moved away from one another. In a method variant, the second and third spacers are joined with mechanical vibration of the spacers or of the first or second layer each connected thereto. The second and third spacers are preferably shaped identically, and in particular have a semi-spherical, conical, tear-shaped, cylindrical, or square outer contour (shape), or an outer contour (shape) in the form of a hyperboloid of one sheet. In this method alternative too, the composite formed of spacers and the first and second layer is preferably heated before the first and second layer are moved away from one another and is preferably cooled or chilled once said layers have been moved away from one another.

Taking into account the aforementioned difference, the embodiments and explanations of the method according to the first alternative of the method can be transferred analogously to the method according to the second alternative. Here, the spacers formed of second and third spacers correspond to the first spacers. Reference is hereby made to the corresponding parts of the description. Of cause, the disclosed methods can be produced with a plurality of layers distanced by means of spacers in accordance with the first and second alternative film elements. To this end, the respective method is implemented a number of times in succession, wherein the first layer provided for example is already a film element consisting of two or more layers.

In accordance with a further exemplary embodiment of the instrument, the tactile sensor at the distal end or the tactile sensor together with the distal end can be detachably connected at an electromechanical interface of the instrument to a further part of the instrument. The tactile sensor or the sensor head may advantageously be joined to the other part of the instrument where necessary. The instrument may thus advantageously also be used in an ulterior manner, that is to say without the tactile sensor. The electromechanical interface can be understood to be an electric and fluidic plug connection.

In accordance with a further exemplary embodiment of the instrument, the tactile sensor has regions of different tactile resolution. A region can be understood to mean a partial area of the tactilely sensitive surface of the sensor element. Regions of high and low tactile resolution may advantageously be provided, wherein, in regions in which a particularly high resolution is necessary, this can be achieved without having to take an unnecessarily high number of measurements in regions in which a lower tactile resolution is necessary. The sensor element having different tactile resolutions comprises a non-conductive, resiliently deformable first layer with a first surface, a non-conductive resiliently deformable second layer with a second surface, wherein the first and second surface face one another and are distanced from one another by resiliently deformable spacers formed between the first and second surfaces and are interconnected, one or more resiliently deformable, electrically conductive first lines, which are arranged/fixed on or at the first surface, and resiliently deformable, electrically conductive second lines which are arranged/fixed on or at the second surface, wherein the first and second lines cross at points of intersection. The first/second lines are preferably arranged between the spacers in regions of the first/second surface. This is true in particular for the points of intersection. The first/second lines may also run beneath the spacers however, in portions or in part. The first/second conductors may advantageously form the resistance elements.

The advantageous sensor element is based on the previously described film element. To achieve the tactile resolutions, this is supplemented by first and second resiliently deformable, electrically conductive lines, which are arranged on or at the first or second surface, wherein the first and second lines cross at points of intersection. As a result of this arrangement of resiliently deformable electrically conductive lines, the film element advantageously supplements the two-dimensional tactile sensor element, which uses the specific resilient deformability and the structure of the film element to improve the direction-dependent resolution when detecting tactile stimuli.

The direction-dependant (anisotropic) resilient deformability of the film element can be set during the production process by a suitable selection of the resilient materials involved (for the first and second layer, for the spacers, and for the resilient lines), by suitable selection of the shape of the spacers, of the arrangement thereof and of the mass thereof, and by a suitable selection of the distance by which the first and second surface are distanced from one another. In the present case, the direction-dependant sensitivity of the sensor element in terms of the detection of tactile stimuli is also determined with the direction-dependent resilient deformability of the film element. The sensor element can thus be designed accordingly depending on the requirement of the resolution of tactile stimuli.

In a simple embodiment of the sensor element, the spacers are arranged between the first and second surface as grid points of a two-dimensional orthogonal grid, in particular a Cartesian grid. In this case, the first lines are preferably arranged parallel to one another and the second lines are preferably arranged parallel to one another, whilst the first and second lines run orthogonally to one another. Of course, any other arrangements of the spacers are possible, for example with a concentric rectangular geometry, with a corresponding arrangement of the first and second lines depending on the objective. Furthermore, the resilient spacers themselves can assume practically any shapes, for example they may be dot-shaped, star-shaped, elongate, or linear, or may have closed shapes, such as circles, ellipses, etc.

The two-dimensional tactile resolution of the sensor element is determined by the areal density of the points of intersection, in particular the points of intersection arranged between the spacers. Each point of intersection constitutes a sort of tactile sensor cell. If the areal density of the points of intersection is large in an areal region, the two-dimensional tactile resolution of the sensor element for this areal region is thus high. If the areal density of the points of intersection is small in an areal region, the two-dimensional tactile resolution of the sensor element for this areal region is thus low.

In one embodiment of the sensor element, the first and second lines are distanced from one another at the points of intersection in a mechanically unstressed state of the sensor element. The expression "mechanically unstressed state" means that no tactile stimuli (forces) are acting on the sensor element.

The first and second lines approach one another at the points of intersection as a result of a force (tactile stimulus) applied to the sensor element, and with continued approach could lead to contact between said lines, and with further continued approach could lead to a resilient deformation of the first and second lines. This approach of the first and the second lines at the points of intersection has effects which can be measured capacitively and/or which affect the electrical conductivity of the first and second lines and by means of which the introduced tactile stimuli can be evaluated in a known manner. If the force applied disappears, the "mechanically unstressed state" is set with a direction-dependant, known, controllable hysteresis to be taken into account when evaluating the above-described measurable effects.

In an alternative embodiment of the sensor element, the first and second lines already contact one another at the points of intersection in the mechanically unstressed state of the sensor element. By applying an external mechanical force (tactile stimulus) to the sensor element, the first and second lines are then resiliently deformed at the respective points of intersection in question, which in each case results in a measurable change to the electrical conductivity of the lines in question.

The first and second layer and the spacers preferably consist of a polymer material, in particular of a silicone material. Furthermore, the first and second lines preferably consist of an electrically conductive polymer material, such as cis-polyacetylene (PA), trans-polyacetylene (PA), or poly-para-phenylene (PPP). Alternatively, the first and second lines may each consist of a non-conductive and resiliently deformable line member with electrically conductive particles incorporated therein.

The first and/or second layer preferably have/has a layer thickness of <30 mm, <15 mm, <10 mm, <5 mm, <2 mm, <1 mm, <0.5 mm, <0.1 mm, or <0.05 mm. Depending on the application, the sensor element consisting of a first and second layer and spacers arranged therebetween has a thickness of <50 mm, <25 mm, <10 mm, <5 mm, <2 mm, <1 mm, <0.5 mm, or <0.1 mm. Furthermore, the distance between the first and second surface is preferably <15 mm, <10 mm, <5 mm, <3 mm, <2 mm, <1 mm, <0.5 mm, <0.2 mm, <0.1 mm, or <0.05 mm. The first and second surface may be distanced from one another by a two-dimensionally constant distance, although this distance may also vary two-dimensionally, depending on the application and objective. In a particularly preferred embodiment, the spacers are arranged as grid points of a two-dimensional Cartesian grid, which has a grid constant in the region of: <10 mm, <5 mm, <3 mm, <1 mm, <0.5 mm, <0.1 mm, <0.05 mm or <0.01 mm.

The gaps between the spacers and the first and second surface are preferably filled by a fluid medium, wherein, in the present case, a fluid medium is understood to mean a substance that does not pose any resistance to an arbitrarily slow shear force and thus has finite viscosity. Fluid media therefore comprise gases and liquids in particular, but also gels. Furthermore, the gaps in the film element may be open or closed on the whole with respect to a surrounding environment of the film element, that is to say in the first case the fluid medium can escape from the film element or can penetrate said film element, and in particular the outer pressure (for example the atmospheric pressure) is identical to the inner pressure in the gaps, and in the second case the fluid medium is trapped in the gaps. The selection of the fluid medium and the embodiment (outwardly closed/open gaps) influence the resilient properties of the film element and can be selected according to the requirements.

A particularly preferred development of the sensor element is characterised in that the sensor element is formed from a plurality of sensor elements arranged one above the other, that is to say a plurality of film elements advantageously equipped with electrical lines are arranged one above the other.

An evaluation module or an evaluation unit is assigned to the sensor element in the form of wiring and can be connected to the first and second lines, wherein the evaluation module or the evaluation unit comprises a capacitance measurement module, with which electrical capacitance changes at individual points of intersection between the first and second lines can be established, and/or comprises a resistance measurement module, with which an electrical contact resistance at individual points of intersection of the first and second lines can be established, and/or comprises a resistance measurement module, with which the electrical line resistances of the individual first and second lines can be established. The location or the affected area of the tactile stimulus on the sensor element as well as the application of force associated with the tactile stimulus can be established from the established capacitance changes or contact resistance changes or line resistance changes.

An advantageous method for producing a sensor element for detecting tactile stimuli comprises the following method steps: providing a resiliently deformable first layer with a first surface, applying first spacers made of a curable polymer material in a first arrangement to the first surface, applying one or more resiliently deformable, electrically conductive first lines to or at the first surface, providing a resiliently deformable second layer with a second surface, applying a plurality of resiliently deformable, electrically conductive second lines to or at the second surface, joining the second surface to the first spacers, at the end thereof remote from the first surface, wherein the first and second lines cross at points of intersection, moving the first and second layer away from one another such that the first and second surface are arranged at a predefined distance from one another and the spacers connect the first and second surface, curing the spacers, wherein the polymer material of the spacers remains resiliently deformable after curing and the spacers, in a mechanically unstressed state, distance the first and second surface by a distance A.

In a development of the above method, one or more resiliently deformable, electrically conductive first lines are first applied to or at the first surface, and the first spacers made of a curable polymer material are then applied in a first arrangement to the first surface, wherein the spacers may also be applied in part to the first lines already provided. The spacers are preferably applied individually, that is to say not contacting one another. Furthermore, the first and second lines are preferably applied to the respective surfaces in such a way that they are arranged between the spacers in the finished sensor element.

An advantageous alternative method for producing the sensor element for detecting tactile stimuli comprises the following method steps: providing a resiliently deformable first layer with a first surface, applying second spacers made of a curable polymer material in a second arrangement to the first surface, applying one or more resiliently deformable, electrically conductive first lines to or at the first surface, providing a resiliently deformable second layer with a second surface, applying third spacers made of a curable polymer material in a third arrangement, which is axially symmetric relative to the second arrangement, to the second surface, applying one or more resiliently deformable, electrically conductive second lines to or at the second surface, aligning the first and second layer so that the arrangements of the second and third spacers applied to the first and second surface are congruently opposed, joining the congruently opposed second and third spacers at their respective free ends, moving the first and second layer away from one another so that the first and second surface are arranged at a predefined distance from one another and the spacers connect the first and second surface, and curing the spacers, wherein the polymer material of the spacers is resiliently deformable after curing and the spacers, in a mechanically unstressed state, distance the first and second surface by a distance A.

In a development of the above method, one or more resiliently deformable, electrically conductive first/second lines are first applied to or at the first/second surface respectively, and the second/third spacers made from a curable polymer material are then applied in a second/third arrangement to the first/second surface respectively, wherein the second/third spacers can also be applied in part respectively to the first/second lines already provided. Note: the first spacers and the composite formed of second and third spacers will each also be referred to hereinafter in a simplified manner as "spacers".

The spacers are preferably applied individually, that is to say not contacting one another. Furthermore, the first and second lines are preferably applied to the respective surfaces in such a way that they are arranged between the spacers in the finished sensor element. This applies to the points of intersection in particular.

In addition, the resiliently deformable, electrically conductive first and second line are applied to the first or second surface respectively before the first and second layer are joined accordingly, wherein the first and second lines cross at points of intersection. Depending on the selection of the thickness of the lines and of the distance, it is possible to determine whether the first and second lines are distanced from one another at the points of intersection in the mechanically unstressed state or whether they contact one another at the points of intersection. The first and second lines preferably consist of an electrically conductive polymer material, such as cis-polyacetylene (PA), trans-polyacetylene (PA), or poly-para-phenylene (PPP). Alternatively, the first and second lines may each consist of a non-conductive and resiliently deformable line member with electrically conductive particles incorporated therein. The first and second line are preferably provided even before their application to the first and second surfaces in a cured state that is to say in a cross-linked, vulcanised, or set state. Alternatively, the first and second lines, similarly to the spacers, may be applied as a curable resilient material and may be cured before the application of the spacers or together with the spacers.

The curable polymer material of the spacers is preferably a thermoplastic material or a silicone material, wherein, in the present case, the term "curable" is understood to mean that the resilient material or the polymer material of the spacers is not yet completely cross-linked, or is not yet completely vulcanised, or is not yet completely set at the moment of application to the first or second surface.

The spacers or the curable resilient material of the electrical lines is preferably applied by means of a pressing, compression-moulding, casting, injection-moulding, doctoring or calendering process. The first surface or the second surface and the spacers applied thereto bond after application of said spacers, although a chemical or physical pretreatment, for example heating of the first/second surface, may be necessary for this purpose.

Depending on requirements, like or different resilient materials can be used for the first layer, the second layer and the spacers to set a predetermined deformation behaviour of the sensor element. The direction-dependant (anisotropic) deformation behaviour of the sensor element can also be set by the selection of the arrangement of the spacers. The arrangement of the spacers preferably has a trapezoidal, annular, elliptical or rectangular, in particular square, geometry. Any other arrangements can of course be implemented depending on requirements. The spacers themselves may assume any shapes that emerge substantially from the requirements for the sensor element. The spacers may thus be cylindrical, wall-like, or cubical, or may be formed as a hyperboloid of one sheet, etc.

Once the spacers have been connected to the first and second surface, the first and second layer are moved away from one another so that the first and second surface are arranged at a predefined distance from one another and the spacers connect the first and second surface. The predefined distance is in any case to be selected so that the spacers also connect the first and second surface, that is to say do not tear or detach from one or both of the first and second surfaces. By moving the first and second layer away from one another, the outer shapes of the spacers are changed. In this case, a cylindrical outer contour of the spacers or an outer contour of the spacers in the form of a hyperboloid of one sheet is typically set. Furthermore, the size of the gaps formed between the first spacers and the first and second surface is also set by moving the first and second layer away from one another. The direction-dependant (anisotropic) deformation behaviour of the film element can in turn be predefined or set by setting the shape of the spacers.

Once the first and second layers have been moved away from one another, the spacers are cured, wherein the polymer material of the spacers is resiliently deformable after curing and the spacers, in a mechanically unstressed state, distance the first and second surface by a distance A. In the present case, the term "curing" is used in the sense of "cross-linking", "vulcanising", "cooling", or "setting" depending on the polymer material used. Once cured, the polymer material of the spacers is resiliently deformable and is substantially dimensionally stable.

In accordance with a further exemplary embodiment of the instrument, the sensor head and the tactile sensor have a shaping. The shaping may advantageously provide the relatively large tactilely sensitive surface. Due to the resilient properties of the tactile sensor, the shaping may be temporarily lost as the instrument is introduced into, or passed through, or removed from the access channel so that the tactile sensor fits through the access channel.

In accordance with a further exemplary embodiment of the instrument, the shaping causes the sensor element to be unfolded or folded depending on a direction of a fluid flow that can be generated by means of the fluid flow source and/or causes the sensor element of the tactile sensor to be rolled up and rolled out. The sensor element may advantageously be unfolded or folded and/or rolled out or rolled up to produce or again reform the tactilely sensitive surface. In this case it is conceivable for the sensor element to be rolled up or rolled out automatically by means of restoring forces due to the shaping and resilient properties. Alternatively and/or additionally, the sensor element may be rolled up and rolled out or unfolded and folded by means of the fluid flow.

In accordance with a further exemplary embodiment of the instrument, the treatment device comprises a tactile display, which is arranged downstream of the tactile sensor and by means of which tactile stimuli picked up by the tactile sensor during the procedure can be displayed. Direct tactile monitoring can thus advantageously be carried out by a person, for example a palpation of tissue and/or a direct monitoring of contact pressures exerted by the instrument on organs.

The object is also achieved with a method for operating a minimally invasive instrument, in particular a minimally invasive instrument of the previously described type. A distal end of the instrument comprising a tactile sensor element is inserted through an access channel having an access channel cross section, and a tactilely sensitive surface of the tactile sensor element with a two-dimensional expansion, which exceeds a dimension of the access channel cross section is then provided. Once the sensor element has been inserted, the relatively large tactilely sensitive surface of the tactile sensor element may advantageously be provided, wherein tactile stimuli can advantageously be picked up by a relatively large area.

The object is also achieved with method for operating a minimally invasive instrument, in particular a minimally invasive instrument of the previously described type, by inserting a distal end of the instrument comprising a tactile sensor element through an access channel having an access cross section, and then providing a tactilely sensitive surface of the tactile sensor element with a two-dimensional expansion, which exceeds a dimension of the access cross section, wherein the sensor element comprises a film element with a first layer and with a second layer distanced from the first layer by means of spacers, and comprises, arranged between the layers of the film element, expansion-sensitive, polymer-based resistance elements for picking up tactile stimuli, picking up the tactile stimuli, wherein the tactile stimuli cause expansions of the polymer-based resistance elements and the expansions of the polymer-based resistance elements cause a change to an electrical conductivity of the polymer-based resistance elements, and converting the change to the electrical conductivity of the polymer-based resistance elements into an electrical resistance signal by means of electrical wiring. The resistance signal is advantageously a measure for the tactile stimuli picked up, or describes said stimuli. The method can be carried out by means of a minimally invasive instrument of the previously described type. The advantages described previously are achieved.

The object is also achieved with a method for operating a minimally invasive instrument, in particular a minimally invasive instrument of the previously described type, by enlarging the sensor head, picking up the tactile stimuli, wherein the tactile stimuli cause expansions of the polymer-based resistance elements and the expansions of the polymer-based resistance elements cause a change to an electrical conductivity of the polymer-based resistance elements, and converting the change to the electrical conductivity of the polymer-based resistance elements into an electrical resistance signal by means of electrical wiring. The resistance signal is advantageously a measure for the tactile stimuli that have been picked up, or described said stimuli. The method can be carried out by means of a minimally invasive instrument of the previously described type. The advantages described previously are achieved.

In an embodiment of the method, a cavity surrounded, at least in part, in a fluid-tight manner by the sensor element is filled with a fluid to enlarge a sensor cross section of the distal end and to provide the tactilely sensitive surface. A hydrostatic pressure can advantageously be built up within the cavity by means of the fluid so that the sensor element adopts a desired shape and size for providing the tactilely sensitive surface.

In a further embodiment of the method, the cavity is emptied, and in doing so the access channel cross section is reduced, and the distal end with the sensor element is then removed through the access channel. The sensor element can advantageously be reduced again after the procedure and removed via the access channel. The sensor element is reduced in particular by means of restoring forces, produced by resilient properties of the sensor element. A negative pressure may also be produced in the cavity, either alternatively or additionally.

In a further embodiment of the method the cavity is filled by means of an inflowing fluid and/or by means of a fluid flow source, and/or the cavity is emptied by means of a discharge of the fluid and/or by means of the fluid flow source. A hydrostatic pressure may advantageously be built up or relieved within the cavity by means of the fluid flow source. Alternatively and/or additionally, the fluid may move due to restoring forces of a shaping or due to the resilient properties of the sensor element. For example, an inflowing fluid can be understood to mean a pressurised fluid flowing out from an opened valve device, for example a gas flowing out from a compressed gas connection or water flowing out from a tap. For emptying, the fluid flow source may generate a fluid flow sucked up from the cavity, that is to say may be operated as a suction pump.

In a further embodiment of the method, the tactile sensor element is stretched to provide the tactilely sensitive surface. The tactile sensor element may advantageously be stretched to enlarge or provide the tactilely sensitive surface. In doing so it is advantageously possible that the tactile sensor element is in a folded state before being stretched, such that it can be slid through the access channel.

Further advantages, features and details will emerge from the following description, in which at least one exemplary embodiment is described in detail, with reference to the drawing where necessary. Features that are described and/or illustrated in the figures belong to the subject of the invention, both individually and in any expedient combination, where applicable also independently of the claims, and in particular may additionally also form the subject of one or more separate applications. Like, similar and/or functionally like parts are denoted by like reference signs.

SUMMARY OF THE DRAWINGS

FIG. 3 shows the plan view illustrated in FIG. 1 of the distal end, wherein the sensor element is illustrated in a provided state of a tactilely sensitive surface, wherein the sensor cross section is enlarged;

FIG. 4 shows a cross section along line IV-IV of the distal end illustrated in FIG. 3;

FIG. 5 shows a view from below the distal end shown in FIG. 3 of the tactilely sensitive surface;

FIG. 6 shows a longitudinal sectional view of a distal end of a further minimally invasive instrument, wherein a tactilely sensitive surface is provided by means of a stretching device;

FIG. 7 shows the sectional view of the distal end shown in FIG. 6, wherein, by contrast, the distal end together with the tactilely sensitive surface is arranged in a folded state within an access channel;

DETAILED DESCRIPTION

Figure 1:
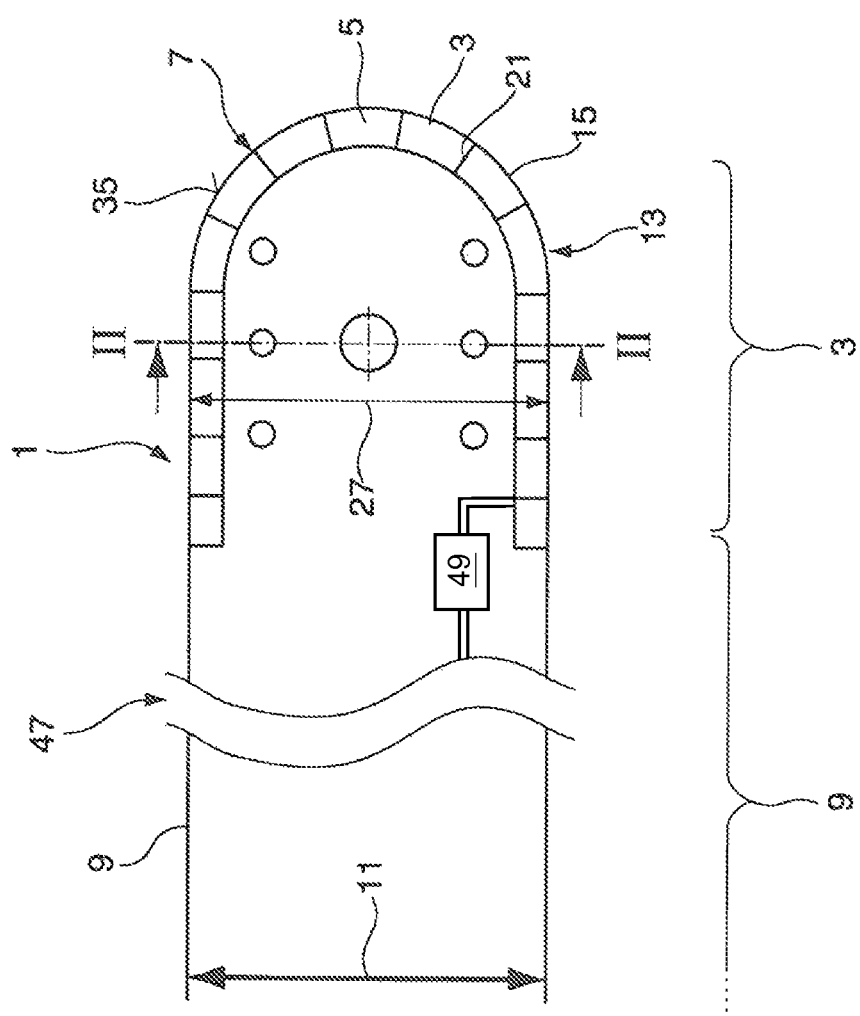
FIG. 1 shows a plan view of a distal end of a minimally invasive instrument with a tactilely sensitive sensor element of a tactile sensor, wherein a sensor cross section of the distal end is minimal.

FIG. 1 shows a plan view of a minimally invasive instrument 1 illustrated merely in part. An enlargeable sensor head of a distal end 3 of the minimally invasive instrument 1 is illustrated. The distal end 3 and the sensor head comprise a tactile sensor 5. Tactile stimuli can be detected by means of the tactile sensor 5. To this end, the tactile sensor 5 comprises a sensor element 7 as well as an evaluation unit 49 arranged downstream of the sensor element 7.

The instrument 1 has a shaft 9, which comprises the distal end 3. The shaft 9 or the distal end 3 of the shaft 9 can be guided through an access channel (not illustrated in greater detail). For example, the access channel may be a natural opening in the body and/or a trocar, which holds open a man-made opening in the body.

The shaft 9 has an instrument cross section and, at the distal end 3, a reduced end cross section, which is characterised by a first dimension. The first dimension is symbolised in FIG. 1 by means of a first double-headed arrow 11 and a second double-headed arrow 27. The instrument cross section and/or the sensor cross section may be characterised for example by a diameter, a width, a height, a surface area and/or a similar dimension. The sensor cross section of the distal end 3 and of the instrument cross section of the shaft 9 are dimensioned such that they can be passed through the access channel (not illustrated in greater detail in FIG. 1), that is to say are smaller than the access channel cross section.

The evaluation unit 49, which is attached to the sensor element 7 or to the resistance elements 21 of the sensor element 7 can be seen in FIG. 1. A change to a conductivity of the polymer-based resistance elements 21 can advantageously be converted into an electrical resistance signal, for example a current or a voltage, by means of the electrical wiring. The change to conductivity is caused by a rotation of the resistance elements 21, which in turn may be caused by the tactile stimulus.

Figure 2:
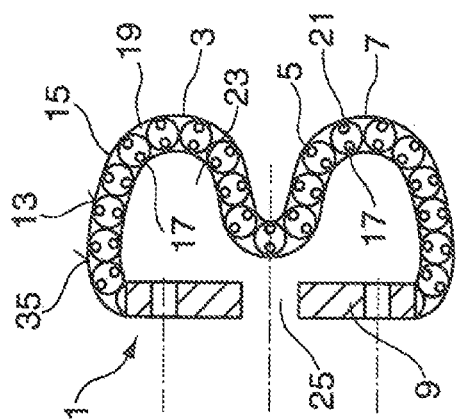
FIG. 2 shows a cross section along line II-II of the distal end illustrated in FIG. 1.

FIG. 2 shows a cross section along line II-II of the distal end 3 of the instrument 1 shown in FIG. 1.

It can be seen that the sensor element 7 has a folded state, wherein the sensor element 7 is folded in a meander-like manner and bears against the distal end 3 of the instrument 1.

The sensor element 7 has a shaping with resilient properties, such that the meander-like folding is reversible, that is to say it can be folded and unfolded, in particular by restoring forces of the shaping, in particular of the folding.

The sensor element 7 of the tactile sensor 5 has a film element 13 with a first layer 15 and with a second layer 17. The layers 15 and 17 are distanced from one another by means of spacers 19. Piezoresistive resistance elements 21, by means of which tactile stimuli are resolvable, are arranged between the layers 15 and 17, that is to say in a gap remaining therebetween. The resistance elements 21 are arranged upstream of the evaluation unit (not illustrated in greater detail).

A cavity 23 is thus produced within an outer face of the shaft 9 and within the film element 13 of the sensor element 7 of the tactile sensor 5. The outer face of the shaft 9, pointing in the direction of an interior of the cavity 23, and the film element 13 of the sensor element 7 of the tactile sensor 5 surround the cavity 23 in a fluid-tight manner. A fluid path 25 discharging into the cavity 23 is assigned thereto. The shaft 9 or the outer face of the shaft 9 has an aperture, wherein the fluid path 25 passes through the aperture in the shaft 9. The fluid-tight cavity 23 can be filled with, or emptied of, a fluid via the fluid path 25. For example, the fluid may be a liquid, in particular water, or a gas, in particular air.

FIGS. 3 and 4 basically show the same illustrations as FIGS. 1 and 2, wherein, by contrast, the cavity 23 is filled via the fluid path 25 with the fluid. It can be seen that the film element 13 of the sensor element 7 thus unfolds or stretches in a balloon-shaped manner due to the effective hydrostatic forces.

Due to the filled cavity 23, the film element 13 adopts an enlarged sensor cross section, wherein the instrument cross section is unchanged. The enlarged sensor cross section has a greater dimension than the sensor cross section illustrated in FIGS. 1 and 2. The second dimension of the enlarged instrument cross section is symbolised in FIG. 3 by means of the double-headed arrow 27. It can be seen that, in the illustrations according to FIGS. 3 and 4, the enlarged sensor cross section is larger than the sensor cross section illustrated in FIGS. 1 and 2, such that the distal end 3 can no longer be guided in a collision-free manner through an access channel 29 illustrated in part and indicated in FIG. 3 merely by means of the reference sign 29 and two lines. In the provided state, the sensor cross section and therefore also a tactilely sensitive surface 35 of the tactile sensor are thus larger than the access channel cross section.

A shaping of the sensor element 7 unfolded in accordance with FIGS. 3 and 4 can be freely selected.

A mechanical stimulus, which acts on the film element 13 of the sensor element 7 of the tactile sensor 5 is symbolised in FIG. 3 by means of an arrow. The mechanical stimulus according to the arrow 31 causes a deformation of the film element 13 and therefore of one of the resistance elements 21 arranged therebeneath accordingly, which in turn can be resolved by means of the evaluation unit (not illustrated in greater detail).

FIG. 5 shows the distal end 3 of the instrument 1 in a view from beneath, wherein the cavity 23 is filled with the fluid, similarly to the illustrations in FIGS. 3 and 4.

The fluid path 25 can be connected to a fluid flow source 33 symbolised in FIG. 4 merely by means of the reference sign 33 in order to fill the cavity 23 with the fluid (not illustrated in greater detail). The cavity 23 can be selectively filled with the fluid or emptied thereof by means of the fluid flow source 33, which in particular may be designed as a bidirectional pump.

The tactilely sensitive surface 35 of the sensor element 7 of the tactile sensor 5 can be seen in FIG. 5. The action of the mechanical stimulus on the tactilely sensitive surface 35 can be seen by means of the arrow 31. The sensor element 7 of the tactile sensor 5 has a first tactile resolution in one region. The sensor element 7 of the tactile sensor 5 may advantageously have a different second tactile resolution in an adjacent region. In particular, the tactile resolution may particularly advantageously be direction-dependant. For example if tissue is passed over in different directions, different sensor signals can thus be obtained, which make it possible to determine more accurately the properties of the tissue.

The second double-headed arrow 27 symbolises that the tactilely sensitive surface 35 also has a two-dimensional expansion, which exceeds the first dimension of the reduced sensor cross section illustrated by means of the second double-headed arrow 27 in FIG. 1. Once the distal end 3 of the instrument 1 has been passed through the access channel 29, a tactilely sensitive surface 35 that is relatively large compared to the cross section of the access channel 29 can thus advantageously be provided. A second dimension of the cross section of the access channel 29 is symbolised in FIG. 3 by means of a third double-headed arrow 37. In this case, it may be a diameter of the access channel 29 for example, but also any other dimension, for example a cross-sectional area, a width, a height and/or the like.

FIGS. 6 and 7 show a further exemplary embodiment of a minimally invasive instrument 1 together with an access channel 29, wherein the instrument 1 is illustrated in FIG. 6 in an unfolded state with a provided and stretched tactilely sensitive surface 35 of the film element 13 of the sensor element 7 of the tactile sensor 5, and the instrument 1 is illustrated in FIG. 7 within the access channel 29 in a folded state with the folded tactilely sensitive surface 35 of the film element 13 of the sensor element 7 of the tactile sensor 5. The access channel 29 may be formed for example by means of a trocar 39.

The distal end 3 of the instrument 1 has a stretching device 41 for stretching the tactilely sensitive surface 35, that is to say for stretching the film element 13 of the sensor element 7 of the tactile sensor 5 of the distal end 3. The stretching device 41 may comprise, for example, pivotable stretching rods 43, which are assigned to the film element 13, are connected to the film element, and stretch said film element by being pivoted away from one another, and vice versa.

Haptic feedback can advantageously be produced during the procedure by means of the instrument 1. This may be advantageous in particular during a minimally invasive intervention.

Alternatively and/or additionally, it is conceivable to arrange a tactile display 45, indicated in FIGS. 6 and 7 merely by means of the reference sign 45, downstream of the tactile sensor 5. In doing so, mechanical stimuli picked up by means of the tactile sensor 5 may advantageously be illustrated by means of the tactile display 45, such that haptic feedback can be produced in spite of the fact that the procedure is carried out indirectly by means of the instrument 1. A two-dimensional distribution of force and/or pressure, which acts over the tactilely sensitive surface 35 of the sensor element 7, can thus be illustrated by means of the tactile display 45 and/or transferred, for example to the fingers of a person operating the minimally invasive instrument 1. A "force feedback" can thus advantageously be implemented during the procedure, alternatively and/or additionally.

The tactile sensor 5 advantageously has flexible properties, so that a palpation and/or surface pressure occurring whilst an organ is lifted for example can advantageously be monitored during the procedure, in particular so as to gauge and/or monitor a perfusion of the organ or to adjust the contact pressure so that it does not pose a risk.

The distal end 3 of the instrument 1 can advantageously be passed through the access channel 29, in particular the access channel 29 of the trocar 39, wherein the greater sensor cross section or a corresponding second diameter advantageously is not limited thereby. Rather, the tactilely sensitive surface 35 may advantageously be enlarged by filling the cavity 23 and/or stretching the stretching device 31 once the distal end 3 of the instrument 1 has been passed through the access channel, such that a relatively large tactilely sensitive surface 35 is provided for examination of relatively large areas, for example for palpation.

The tactile sensor 5 or the sensor element 7 may comprise a polymer-based resilient material.

A hydrostatic pressure, in particular a hydraulic and/or pneumatic pressure, can be applied to the cavity 23 by means of the fluid flow source 33 so as to thus unfold the sensor element 7 or the tactilely sensitive surface 35 of the tactile sensor 5. The tactilely sensitive surface 35 is advantageously limited by the cross section of the access channel 29, in particular of the trocar 39.

Alternatively and/or additionally, a large number of shaped tactile sensors can be produced by an advantageous selection of a geometry of the hollow body 23, in particular so is to adapt said sensors to the procedure in a task-pacific manner. A highly flexible tactile sensor 5 of which the shape can be changed and which can advantageously be used together with the minimally invasive instrument 1 is advantageously produced.

It is alternatively and/or additionally conceivable, in particular by means of the tactile display 45, to enable simultaneous palpation of much larger areas and therefore more reliable detection of smaller and/or larger hardenings in a soft tissue to be examined.

The sensor element 7 or the tactilely sensitive surface 35 of the sensor element 7 has a sensor matrix, which is defined by the three-dimensional cavity 23. The sensor matrix or the tactilely sensitive surface 35 can advantageously be used in a three-dimensional form corresponding spatially to the cavity 23.

It is alternatively and/or additionally conceivable to provide an electromechanical interface 47, by means of which the distal end 3 together with the tactile sensor 5 and/or the tactile sensor 5 can be connected so as to be detachable from the rest of the minimally invasive instrument 1.

It is alternatively and/or additionally conceivable to design the cavity 23 and/or the sensor element 7 so that it can be rolled up and rolled out and/or folded and unfolded.

Figure 8:
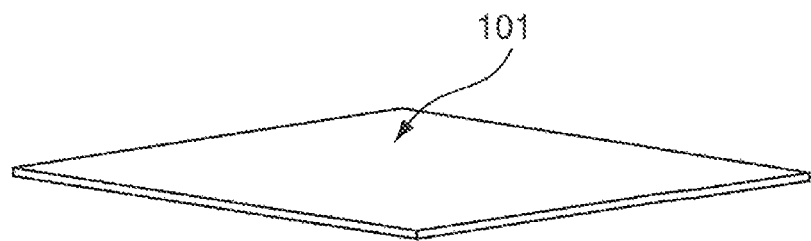
FIG. 8 shows a provided first layer of a film element used for the minimally invasive instrument.

FIG. 8 shows a first method step, in which a first layer 101 with a first surface made of a resiliently deformable material is provided. The first layer 101, in the present case made of a silicone material, can be produced in a compression-moulding, casting, spinning, pressing, dipping, spraying or calendering process. The first layer 101 can be formed as a two-dimensional flat layer or as a layer formed three-dimensionally in space. The layer thickness of the first and/or the second layer 103 may be several millimeters, but also micrometers, depending on the application, for example <500 µm, <300 µm, <200 µm, <150 µm, <100 µm, <75 µm, or <50 µm.

Figure 9:
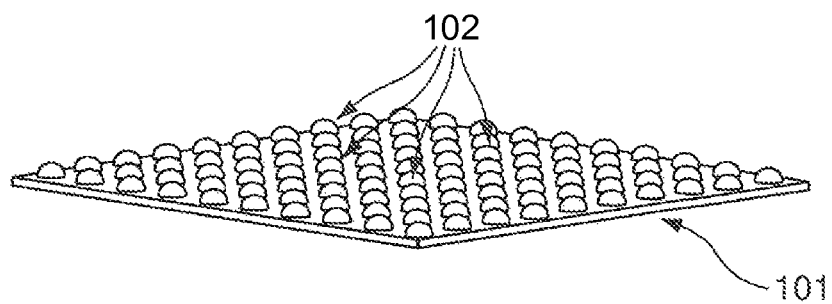
FIG. 9 shows second spacers of the film element applied to the first surface of the first layer.

FIG. 9 shows the first layer 101 once individual second spacers 102 made of a curable polymer material (in the present case a silicone material) have been applied in a second arrangement to the first surface of the first layer 101. It can be clearly seen that the spacers 102 are arranged at a distance from one another that corresponds at least to their diameter. In the present case, silicone bumps in a square arrangement, that is to say at the respective corners of a square, have been applied to the first surface as second spacers.

The provision of the second layer 103 made of a resiliently deformable material with a second surface, and the application to the second surface of individual third spacers 104 made of a curable polymer material, in the present case likewise a silicone material, in a third arrangement axially symmetric relative to the second arrangement are not illustrated.

Figure 10:
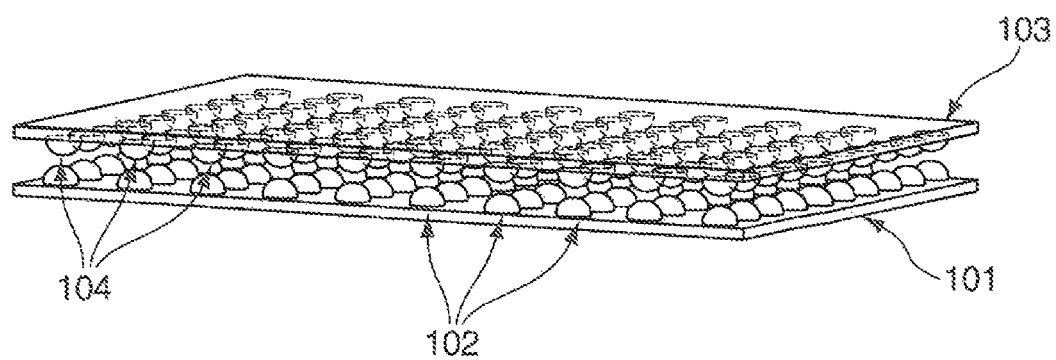
FIG. 10 shows an aligned first and second layer of the film element.

FIG. 10 shows the alignment of the first layer 101 and second layer 103, such that the arrangements of the second spacers 102 and third spacers 104 applied axially symmetrically to the first and second surface are congruently opposed.

Figure 11:
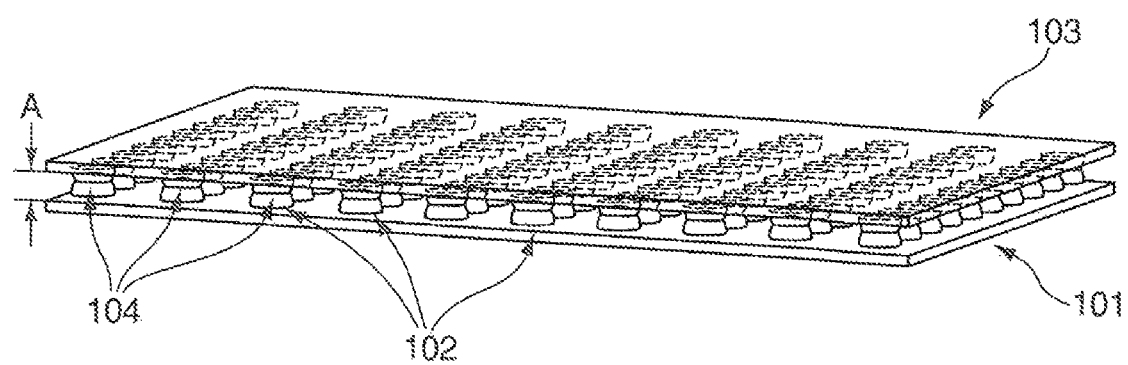
FIG. 11 shows the state when joining the second and third spacers of the film element.

FIG. 11 shows the joining of the congruently opposed second spacers 102 and third spacers 104 at their respective free ends. So as to promote the joining process in the case of thermoplastic materials, the free ends of the second spacers 102 and third spacers 104 have been heated beforehand. The joining process may alternatively or additionally be promoted by means of mechanical vibration of the first layer 101 and second layer 103.

Once the joining process is complete, the second spacers 102 and third spacers 104 are interconnected, and the first layer 101 and second layer 103 are equally interconnected via the connecting spacers 102, 104. In this method step, the connected spacers 102, 104 are present as polymer material that can still be cured, that is to say in the present case as silicone material that has not yet fully cross-linked. The material therefore still has at least a low level of fluidity.

Figure 12:
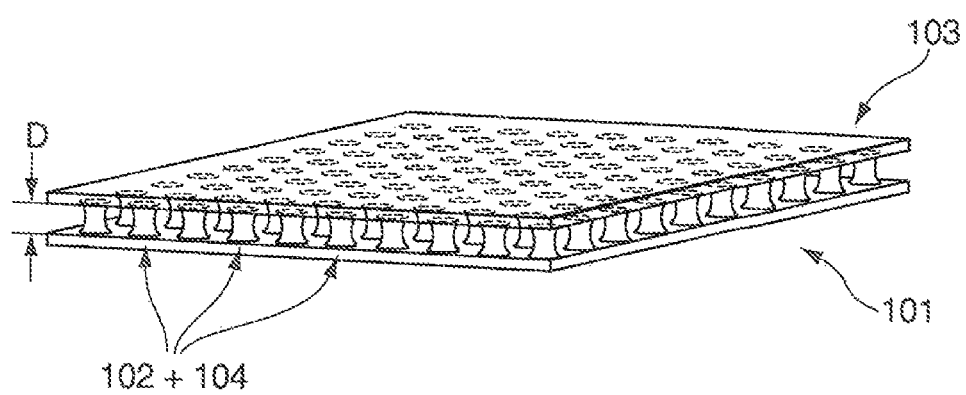
FIG. 12 shows the state once the first and second layer have been moved away from one another until a desired total thickness of the film element has been achieved.

FIG. 12 shows the state of the film element once the first layer 101 and second layer 103 have been moved away from one another, such that the first and second surface are arranged at a predefined distance from one another and the joined spacers 102, 104 connect the first and second surface. It can be clearly seen that, by moving the first and second layer away from one another, the outer contours of the joined spacers 102, 104 have approximated the shape of a hyperboloid of one sheet, of which the central diameter is smaller than the foot diameter at each of the first and second surface.

In a last method step (not illustrated) a curing process also takes place in the present case, that is to say full cross-linking of the silicone material of the joined spacers 102, 104, wherein the polymer material of the joined spacers 102, 104 remains resiliently deformable after curing and the spacers 102, 104, in a mechanically unstressed state, distance the first and second surface by a distance A. The film element has a total thickness D.

Figure 13:
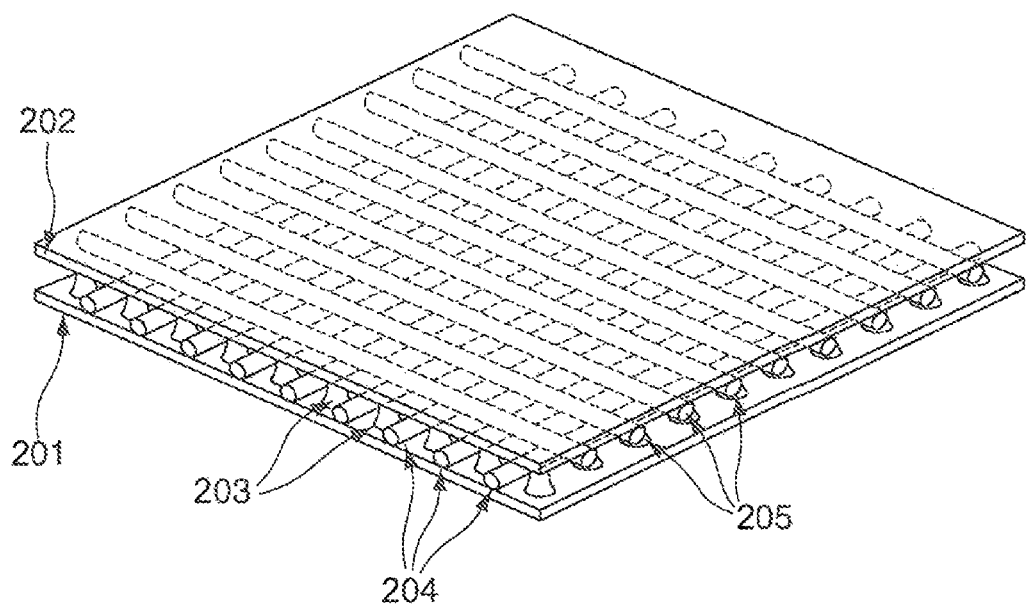
FIG. 13 shows a schematic oblique view of an advantageous sensor element that can be used for the minimally invasive instrument illustrated in FIGS. 1 to 7.

FIG. 13 shows a schematic oblique view of a sensor element of the minimally invasive instrument 1 illustrated in FIGS. 1 to 7. A sensor element with a first layer 201 and with a second layer 202 is illustrated. Depending on the position of installation of the sensor element, either the first surface 201 or the second surface 202 forms the tactilely sensitive surface 35 of the minimally invasive instrument 1 illustrated in FIGS. 1 to 7. Both layers are interconnected via spacers 203 and are distanced from one another by the distance A. The spacers 203 are arranged individually in a square grid shape. First 204 and second 205 electrically conductive resiliently deformable lines run in gaps/cavities between the spacers 203 and the first layer 201 and second layer 202. The first lines 204 run parallel to one another. The second lines 205 likewise run parallel to one another, wherein the first lines 204 and second lines 205 are arranged in an intersecting manner, in the present case orthogonally to one another. Furthermore, the first lines 204 are arranged on the first surface of the first layer 201, and the second lines 205 are arranged on the second surface of the second layer 202. The points of intersection are arranged in regions between the spacers 203. In the mechanically unstressed state, the first lines 204 and second lines 205 intersect at the points of intersection without contacting one another. The first lines 204 and second lines 205 may form the previously described advantageous resistance elements 21.

Due to the use of polymer-based first lines (conductive tracks) 203 and second lines (conductive tracks) 204, the sensor element is resiliently deformable on the whole. It has gaps/cavities between the spacers 203 and the first surface of the first layer 201 and the second surface of the second layer 202, said gaps/cavities being filled with air in the present case. With a corresponding selection of the materials used and layer thicknesses, the sensor element can be designed as a highly flexible, thin and resiliently expandable sensor element. These properties make it possible for the advantageous sensor element to be applied to extremely curved surfaces, such as a gripper finger of a robot hand, a medical instrument for minimally invasive interventions, etc., where it can then imitate the human cutaneous sense of touch, for example so as to thus determine the position, shape, material consistency or surface structure of contacted objects.

The sensor element enables a combined measurement of pressure and expansion due to the detection of various effects. The following effects are used in the process:

1. Change to Electrical Capacitance

An electrical capacitor is formed at each point of intersection of the first lines 204 and second lines 205 between the respective first line 204 and the respective second line. If a tactile stimulus is applied to the sensor element, the sensor element is thus compressed and the first lines 204 and second lines 205 approach one another. The electrical capacitance at the respective point of intersection thus changes. This effect can be detected and evaluated. Due to the specific design of the sensor element with the gaps and the first layer 201 and second layer 202 distanced by the spacers, only very small material volumes have to be deformed in this instance for the first lines 204 and second lines 205 to move closer to one another and thus cause a change to capacitance. A very high level of sensitivity is thus achieved for a tactile stimulus of the sensor element, and therefore even the smallest occurrences of contact can be detected. The change to capacitance at the points of intersection can also be used to identify the points of intersection to which pressure has been applied and to thus detect the distribution of pressure over the sensor element.

2. Electrical Contact Resistance

If the intensity of the tactile stimulus is increased further, the first lines 204 and second lines 205 contact one another at the respective points of intersection. An electrical resistance can thus be measured. With a further increase in the intensity of the stimulus (increase in force or pressure), the first lines 204 and second lines 205 elastically deform at the respective points of intersection. The contact area between the lines at the respective points of intersection and the electrical contact resistance thus changes. This change in resistance can be detected and evaluated for each point of intersection.

3. Electrical Line Resistance in the Lines

If a mechanically soft material is used beneath the sensor element, the effect described in DE 10 2007 020 131 for determining the mechanical expansion can also be detected. In this case, the expansion-dependant change of the electrical line resistance in the lines is detected and evaluated. If the first lines 204 and second lines 205 are produced in a compression-moulding or pressing method for example, the cross section thereof can thus be selected practically arbitrarily. This can be used to linearize the transfer function of the effect described under point 2. The first lines 204 and second lines 205 used in the X-direction and Y-direction are in the present case separated spatially from one another by the spacers 203 in the mechanically unstressed state of the sensor element.

Figure 14:
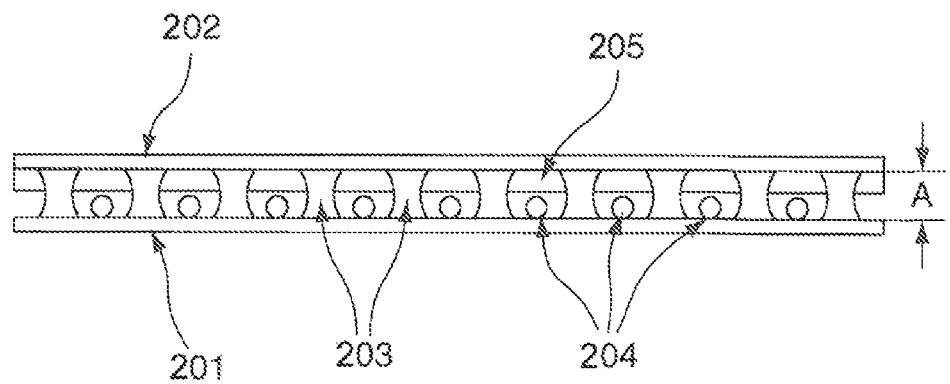
FIG. 14 shows a schematic side view of the sensor element from FIG. 13.

FIG. 14 shows a schematic side view of the sensor element of FIG. 1 in a mechanically unstressed resting state, that is to say in a state of the sensor element when no tactile stimulus is introduced. The spacers 203, which have an outer contour in the form of a hyperboloid of one sheet due to the fact that the first layer 201 and second layer 202 have been moved away from one another during the production process, can be clearly seen. The first and second surface are distanced from one another by a distance A. It can also be clearly seen that the first lines 204 and second lines 205 do not contact one another at the points of intersection.

Figure 15:
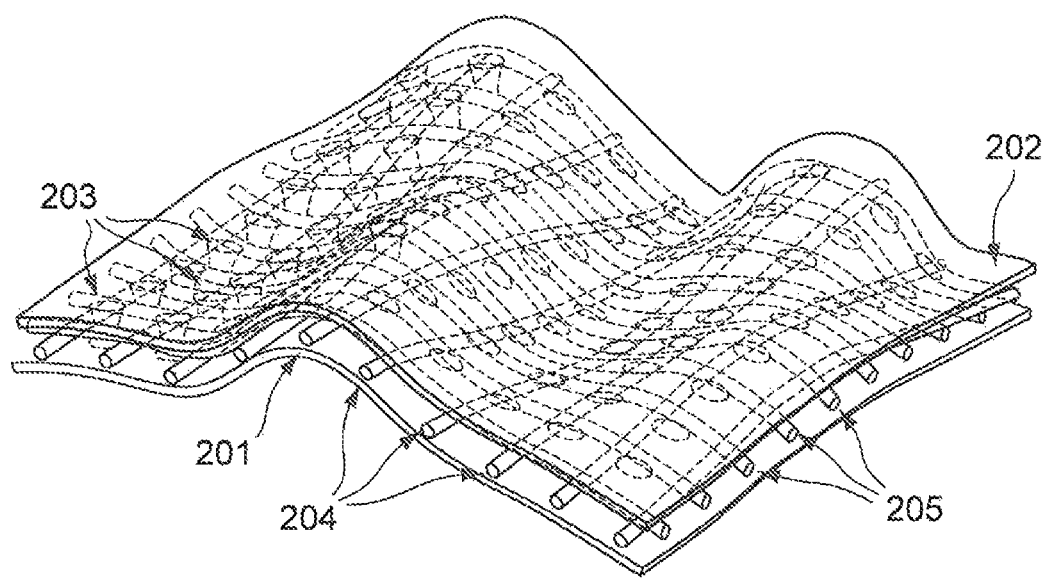
FIG. 15 shows a schematic illustration of the sensor element from FIGS. 13 and 14 for use over a three-dimensionally shaped surface.

FIG. 15 shows a schematic illustration of the sensor element from FIGS. 1 and 2 for use over a three-dimensionally shaped surface. Due to the elastic deformability of the sensor element as a whole, three-dimensionally shaped surfaces, such as a gripper, a robot finger, etc. can also be equipped with the two-dimensional tactile sensor element.

LIST OF REFERENCE SIGNS 1 minimally invasive instrument
3 distal end
5 tactile sensor
7 sensor element
9 shaft
11 double-headed arrow
13 film element
15 first layer
17 second layer
19 spacer
21 resistance element
23 cavity
25 fluid path
27 double-headed arrow
29 access channel
31 arrow
33 fluid flow source
35 tactilely sensitive surface
37 double-headed arrow
39 trocar
41 stretching device
43 stretching rods
45 tactile display
47 electromechanical interface
49 evaluation unit
101 first layer
102 second spacer
103 second layer
104 third spacer
A distance between the first and second surface
D total thickness of the film element
201 resiliently deformable, electrically non-conductive first layer 202 resiliently deformable, electrically non-conductive second layer
203 spacer
204 resiliently deformable, electrically conductive first lines
205 resiliently deformable, electrically conductive second lines

The invention claimed is:

1. An instrument associated with measuring tactile stimuli of an internal organ, the instrument comprising:
   a shaft having a distal end;
   an enlargeable sensor head connectable to the distal end of the shaft and having an interior cavity, the enlargeable sensor head comprising a sensor element having resilient properties, the sensor element comprising:
      a first elastic layer;
      a plurality of spacers; and
      a second elastic layer distanced from the first elastic layer by the plurality of spacers; and
   a plurality of expansion-sensitive resistance elements to measure the tactile stimuli of the internal organ, each of the plurality of expansion-sensitive resistance elements arranged between the first layer and the second layer, and further arranged between a respective set of spacers, wherein electrical resistance of the expansion-sensitive resistance elements varies dependent on their expansion and contraction as a result of the interior cavity of the enlargeable sensor head expanding and contracting, respectively.

2. The instrument according to claim 1, wherein the instrument comprises an electromechanical interface configured to connect the enlargeable sensor head to the distal end of the shaft.

3. The instrument according to claim 1, wherein the sensor head includes a stretching device configured to transfer the sensor element from an expanded state into a contracted state, and vice versa.

4. The instrument according to claim 1, wherein the interior cavity is surrounded in a fluid-tight manner by the sensor element and the shaft.

5. The instrument according to claim 4, wherein the instrument further comprises a fluid path that connects a fluid flow source to the interior cavity.

6. The instrument according to claim 5, wherein the fluid flow source is configured to expand the enlargeable sensor head by charging fluid into the interior cavity.

7. The instrument according to claim 5, wherein the fluid flow source is configured to contract the enlargeable sensor head by discharging fluid from the interior cavity.

8. The instrument according to claim 1, wherein the sensor element comprises regions having different tactile resolutions.

9. The instrument according to claim 1, further comprising a tactile display device to display measurement results of the tactile stimuli as measured.

10. A method of operating the instrument according to claim 1, the method comprising:
    inserting the distal end through an access channel into a measuring position associated with the internal organ;
    charging fluid into the internal cavity to enlarge the enlargeable sensor head;
    determining electrical conductivity signals of the plurality of expansion-sensitive resistance elements to measure the tactile stimuli of the internal organ; and
    evaluating the electrical conductivity signals using an evaluation unit.

11. The method of claim 10, wherein the method further comprises:
    discharging the fluid from the interior cavity; and
    removing the distal end through the access channel.

12. The method of claim 10, wherein the method further comprises displaying the electrical conductivity signals as evaluated.

* * * * *